United States Patent
Fu

(10) Patent No.: US 12,064,444 B2
(45) Date of Patent: Aug. 20, 2024

(54) APPLICATION OF TANNIC ACID IN PREPARATION OF MEDICAMENT AGAINST RESPIRATORY VIRUSES

(71) Applicant: SUNTRAP LIFE TECHNOLOGIES LTD., Guangdong (CN)

(72) Inventor: Jun Fu, Guangdong (CN)

(73) Assignee: SUNTRAP LIFE TECHNOLOGIES LTD., Guangdong (CN)

( * ) Notice: Subject to any disclaimer, the term of this patent is extended or adjusted under 35 U.S.C. 154(b) by 0 days.

(21) Appl. No.: 17/630,512

(22) PCT Filed: Sep. 10, 2020

(86) PCT No.: PCT/CN2020/114432
§ 371 (c)(1),
(2) Date: Jan. 27, 2022

(87) PCT Pub. No.: WO2022/036774
PCT Pub. Date: Feb. 24, 2022

(65) Prior Publication Data
US 2022/0354877 A1 Nov. 10, 2022

(30) Foreign Application Priority Data
Aug. 17, 2020 (CN) .......................... 202010826586.2

(51) Int. Cl.
| | | |
|---|---|---|
| A61K 31/14 | (2006.01) | |
| A61K 9/00 | (2006.01) | |
| A61K 9/12 | (2006.01) | |
| A61K 31/05 | (2006.01) | |
| A61K 31/353 | (2006.01) | |
| A61K 31/7034 | (2006.01) | |
| A61K 33/06 | (2006.01) | |
| A61K 33/24 | (2019.01) | |
| A61K 33/26 | (2006.01) | |
| A61K 33/30 | (2006.01) | |
| A61P 31/14 | (2006.01) | |

(52) U.S. Cl.
CPC ........ *A61K 31/7034* (2013.01); *A61K 9/0053* (2013.01); *A61K 9/12* (2013.01); *A61K 31/05* (2013.01); *A61K 31/353* (2013.01); *A61K 33/06* (2013.01); *A61K 33/24* (2013.01); *A61K 33/26* (2013.01); *A61K 33/30* (2013.01); *A61P 31/14* (2018.01)

(58) Field of Classification Search
CPC .. A61K 31/7034; A61K 31/05; A61K 31/353; A61K 31/30; A61K 31/7024; A61K 9/0053; A61K 9/12; A61K 33/06; A61K 33/24; A61K 33/26; A61K 33/30; A61K 33/00; A61P 31/14; A23K 20/24; A23K 20/163; A23K 50/20; A23K 50/30; A23K 50/40; A23K 50/50; A23K 50/75; A23K 50/70; A23L 33/10; A23V 2002/00
See application file for complete search history.

(56) References Cited

U.S. PATENT DOCUMENTS 4,339,438 A * 7/1982 Fahim ................... A61K 31/19
514/533

FOREIGN PATENT DOCUMENTS

| CN | 105535012 | | 5/2016 |
|---|---|---|---|
| CN | 105687226 | | 6/2016 |
| CN | 109745354 | | 5/2019 |
| CN | 111297838 A | * | 6/2020 |
| JP | 2011084549 | | 4/2011 |

OTHER PUBLICATIONS

He et al., Potential of coronavirus 3C-like protease inhibitors for the development of new anti-SARS-COV-2 drugs: Insights from structures of protease and inhibitors, Jun. 6, 2020, International Journal of Antimicrobial Agents, vol. 56 iss. 2, pp. 1-10. (Year: 2020).*
Farshi et al., A comprehensive review on the effect of plant metabolites on coronaviruses: focusing on their molecular docking score and IC50 values, May 18, 2020, Preprints, pp. 1-60. (Year: 2020).*
Gonzalez et al., Intravenous Vitamin C and an Orthomolecular Protocol as Therapy for COVID19: A Case Report, Aug. 1, 2020, Journal of Orthomolecular Medicine, vol. 35 iss. 1, pp. 1-3 (Year: 2020).*
Michael Wink, "Potential of DNA Intercalating Alkaloids and Other Plant Secondary Metabolites against SARS-CoV-2 Causing COVID-19", Diversity 2020, 12(5), Apr. 30, 2020, pp. 1-12.

(Continued)

*Primary Examiner* — Ali Soroush
(74) *Attorney, Agent, or Firm* — JCIPRNET

(57) ABSTRACT

The present invention provides an application of tannic acid in preparing a medicament against respiratory viruses. The present invention show through live virus experiments that tannic acid has a significant inhibitory effect on respiratory viruses including SARS-CoV-2 coronavirus, Influenza A H1N1 virus, etc., with an exact curative effect, and thus has a broad application prospect in the field of preparation of medicaments against respiratory viruses. In addition, tannic acid exists in a variety of plants, which is a natural active compound existing in nature, and has also been used as a food additive, with a high safety and good foundation for medicament development.

8 Claims, No Drawings

(56) References Cited

OTHER PUBLICATIONS

Ibrahim Khalifa, et al., "Tannins inhibit SARS-CoV-2 through binding with catalytic dyad residues of 3CLpro: An in silico approach with 19 structural different hydrolysable tannins", Journal of Food Biochemistry, Aug. 11, 2020, pp. 1-19.

Xiao Lan, "Fighting against SARS and protecting health", Medicine Economic Reporter, May 28, 2003, pp. 1-3.

Soodeh Mahdian, et al., "Drug repurposing using computational methods to identify therapeutic options for COVID-19", Journal of Diabetes & Metabolic Disorders, May 30, 2020, pp. 1-9.

Zhou Yi-Bo, et al., "Traditional Chinese medicines targeting influenza virus replication: research progress", J Int Pharm Res, vol. 46, No. 5, May 31, 2019, pp. 1-7.

Li Ping, et al., "The effects of resveratrol on antibacterial and antiviral properties", Chinese Journal of Microecology, vol. 26, No. 10, Oct. 31, 2014, pp. 1215-1219.

Xiang Qian, et al., "Characteristics and prevention of coronavirus infection", Chinese Journal of Nosocomiology, 013(011):1097-1100, 2003, pp. 1-5.

Chia-Nan Chen, et al., "Inhibition of SARS-CoV 3C-like protease activity by theaflavin-3, 3'-digallate (TF3)", Evid Based Complement Alternat Med., 2(2), Apr. 7, 2005, pp. 209-215.

"Office Action of China Counterpart Application", with English translation thereof, issued on Nov. 14, 2020, p. 1-p. 11.

"International Search Report (Form PCT/ISA/210)" of PCT/CN2020/114432, mailed on May 13, 2021, pp. 1-5.

\* cited by examiner

APPLICATION OF TANNIC ACID IN PREPARATION OF MEDICAMENT AGAINST RESPIRATORY VIRUSES

CROSS-REFERENCE TO RELATED APPLICATION

This application is a 371 of international application of PCT application serial no. PCT/CN2020/114432, filed on Sep. 10, 2020, which claims the priority benefit of China application no. 202010826586.2, filed on Aug. 17, 2020. The entirety of each of the above-mentioned patent applications is hereby incorporated by reference herein and made a part of this specification.

TECHNICAL FIELD

The invention relates to the technical field of biomedicine, and more specifically relates to an application of tannic acid in preparation of a medicament against respiratory viruses.

BACKGROUND

Diseases caused by viruses are basically contagious to a certain extent, and their outbreaks or epidemics will have a huge impact on human health and life. Currently, the prevention and treatment of viral infections mainly relies on vaccination and/or antiviral medicament treatment. However, in clinical applications, vaccines are relatively expensive and require low-temperature storage, which makes it difficult to be widely used; on the other hand, many current viruses have variability, especially respiratory viruses (such as coronaviruses, Orthomyxoviridae viruses, etc.) are more prone to mutation, and it is difficult for vaccine development to keep up with the mutation of the viruses. Therefore, antiviral medicaments have gradually become a main means of treating viral infectious diseases.

Among them, the coronaviruses in respiratory viruses belong to order Nidovirales, family Coronaviridae, and genus Coronavirus in genealogical classification. Viruses of the genus Coronavirus are RNA viruses with an envelope and a linear single positive-stranded genome, being a large class of viruses widespread in nature. The coronaviruses have a diameter of about 80 to 120 nm, a methylated cap-like structure at a 5' end of the genome, a poly(A) tail at a 3' end, and a full-length genome of about 27 to 32 kb, being the viruses with the largest genome among the known RNA viruses. The coronaviruses only infect vertebrates, including humans. Currently known coronaviruses that infect humans and cause great epidemics include SARS-CoV, SARS-CoV-2, MERS-CoV, HCoV-229E, HCoV-NL63, HCoV-0C43, and HCoV-HKU1, which can cause diseases of respiratory tract, digestive tract, liver and nervous system. Human coronaviruses were isolated in 1965, but until now knowledge about them is still quite limited, and a serotype and antigenic variability of coronaviruses are unclear. In addition, the coronavirus can cause repeated infections, indicating that there are multiple serotypes (at least 4 types known) and antigenic variation. Its immunity is difficult, and there are no specific preventive and therapeutic medicaments.

At present, only experimental studies have found that a zauracil, ribavirin (Virazole), and spiroadamantane have obvious inhibitory effects on the coronaviruses (XIANG Qian, WANG Rui. Characteristics and prevention of coronavirus infection[J]. Chinese Journal of Nosocomiology, 2003, 013(011):1097-1100.). However, the above-mentioned medicaments are prone to adverse reactions such as diarrhea, anemia, dizziness, headache, weakness and fatigue. In addition, clinical studies have found that Remdesivir (CAS: 1809249-37-3) has certain activity against Coronaviridae viral pathogens such as atypical pneumonia (SARS) and Middle East respiratory syndrome (MERS), but Remdesivir has not been approved for marketing in any countries, and its safety and efficacy have not been proven. It can be seen that the current anti-coronavirus medicaments all have certain safety hazards, and with the mutation of the viruses and an emergence of new strains, an antiviral effect of these chemical medicaments is greatly reduced. For example, for a novel coronavirus 2019-nCoV (SARS-CoV-2) that appeared at the end of 2019, no medicament with an exact curative effect has yet been found until now.

SUMMARY OF THE INVENTION

A technical problem to be solved by the present invention is to overcome defects and deficiencies of the existing medicaments against respiratory viruses, and provide a new selection of a medicament against respiratory viruses, namely tannic acid (CAS: 1401-55-4). After extensive explorations and researches, inventors found that tannic acid has a significant antiviral effect on respiratory viruses, especially on coronaviruses and Orthomyxoviridae influenza viruses. And this kind of substance exists in a variety of plants, which is a natural active compound existing in nature, and has also been used as a food additive, with a high safety, and thus it has a good application prospect in preparation and development of antiviral medicaments against respiratory viruses.

An objective of the present invention is to provide an application of tannic acid in preparation of a medicament against respiratory viruses.

Another objective of the present invention is to provide an application of a tannic acid derivative or a tannic acid structural analog in preparation of a medicament against respiratory viruses.

Another objective of the present invention is to provide a medicament against respiratory viruses including tannic acid.

The above-mentioned objectives of the present invention are achieved through the following technical solutions.

Researches of the present invention show that tannic acid has a significant antiviral effect on respiratory viruses, especially its inhibitory effect on a novel coronavirus 2019-nCoV (SARS-CoV-2) is significantly higher than that of a positive control drug Remdesivir, and its antiviral effect on Orthomyxoviridae influenza viruses is also very significant. Based on the above achievements, the present invention claims an application of tannic acid in preparation of a medicament against respiratory viruses.

The tannic acid of the present invention exists in a free form, or, as appropriate, as a pharmaceutically acceptable derivative. According to the present invention, the pharmaceutically acceptable derivatives include, but are not limited to, pharmaceutically acceptable promedicaments, salts, esters, salts of esters, or any other adducts or derivatives that can be administered directly or indirectly according to patients' needs, compounds described in other aspects of the invention, metabolites or residues thereof.

Therefore, the present invention further claims the application of tannic acid derivatives or tannic acid structural analogs in the preparation of a medicament against respiratory viruses.

Further, stereoisomers, geometric isomers, hydrates, solvates or pharmaceutically acceptable salts or promedicaments of tannic acid, tannic acid derivatives, and tannic acid structural analogs should also be within protection scope of the present invention.

The "solvate" of the present invention refers to an association compound formed by one or more solvent molecules with a compound of the present invention. Solvents forming the solvate include, but are not limited to, water, isopropanol, ethanol, methanol, dimethylsulfoxide, ethyl acetate, acetic acid, and aminoethanol. The term "hydrate" refers to an association compound formed by a solvent molecule which is water.

Further, the respiratory viruses include Coronaviridae viruses and Orthomyxoviridae viruses.

Further, the Coronaviridae viruses are Coronavirus viruses.

The Coronavirus viruses currently confirmed include SARS-CoV, SARS-CoV-2, MERS-CoV, HCoV-229E, HCoV-NL63, HCoV-0C43, and HCoV-HKU1.

Preferably, the Coronavirus virus is SARS-CoV-2.

Further, the Orthomyxoviridae viruses include Influenza A viruses, Influenza B viruses, and Influenza C viruses.

Preferably, the Orthomyxoviridae virus is an Influenza A H1N1 virus belonging to the Influenza A viruses.

Based on this, the present invention further provides a medicament against respiratory viruses, including tannic acid.

Further, the medicament further includes any one or two of tannic acid derivatives and tannic acid structural analogs.

Further, the medicament further includes one or two of polyphenolic compounds and antiviral metal salts.

Further, the antiviral metal salts include zinc salts, iron salts, calcium salts, magnesium salts, tungsten salts and rubidium salts.

Preferably, the zinc salt is zinc sulfate or zinc gluconate; the iron salt is ferrous gluconate; the calcium salt is calcium gluconate; the tungsten salt is sodium tungstate; and the rubidium salt is rubidium iodide.

Further, a mass ratio of the tannic acid, the tannic acid derivative or the tannic acid structural analog to the antiviral metal salt is 1:0.05 to 1:50.

Even further, the polyphenolic compounds include flavonoids, stilbene, phenolic acids, lignans, and the like.

Further, a mass ratio of the tannic acid, the tannic acid derivative or the tannic acid structural analog to the polyphenolic compound is 1:0.05 to 1:50.

It is claimed in the present invention the application of the compounds or compositions in preparation of medicaments against respiratory viruses, which is not limited to, the application in preparation of medicaments for preventing or treating diseases caused by respiratory viruses, alleviating symptoms of diseases caused by respiratory viruses, or delaying development or onset of diseases caused by respiratory viruses, by administering the compounds or compositions of the present invention in an effective amount to patients.

The compounds or medicaments claimed in the present invention, in addition to their therapeutic benefits in humans, can further be used in veterinary treatment of pets, introduced species of animals and farm animals, including mammals, rodents, poultry, and the like. Examples of additional animals include horses, dogs, cats, pigs, and the like.

Further, the medicament further includes a pharmaceutically acceptable adjuvant, carrier, excipient, diluent, vehicle, etc., which is prepared into different pharmaceutical dosage forms, such as an injection, an oral preparation, a spray, an inhalant, an aerosol, etc.

Substances that can be used as the pharmaceutically acceptable carriers include, but are not limited to, an ion exchanger, aluminum, aluminum stearate, lecithin, serum protein such as human serum albumin, a buffer substance such as a phosphate, glycine, sorbic acid, potassium sorbate, a partial glyceride mixture of saturated vegetable fatty acids, water, a salt or an electrolyte such as protamine sulfate, disodium hydrogen phosphate, potassium hydrogen phosphate, sodium chloride, a zinc salt, colloidal silicon, magnesium trisilicate, polyvinylpyrrolidone, polyacrylate, wax, polyethylene-polyoxypropylene-blocking polymer, lanolin, a saccharide such as lactose, glucose and sucrose; a starch such as corn starch and potato starch; a cellulose and derivatives thereof such as sodium carboxymethylcellulose, ethyl cellulose and cellulose acetate; gum powder; malt; gelatin; talc powder; an adjuvant such as cocoa butter and suppository wax; oil such as peanut oil, cottonseed oil, safflower oil, sesame oil, olive oil, corn oil, and soybean oil; a glycol such as propylene glycol and polyethylene glycol; an ester such as ethyl oleate and ethyl laurate; agar; a buffer such as magnesium hydroxide and aluminum hydroxide; alginic acid; pyrogen-free water; an isotonic salt; Ringer's solution; ethanol, phosphate buffer solution, and other non-toxic suitable lubricants such as sodium lauryl sulfate and magnesium stearate, a colorant, a release agent, a coating, a sweetener, a flavouring agent and a spice, a preservative and an antioxidant.

To prepare a solid composition such as a tablet, a principal active ingredient is mixed with a pharmaceutical excipient (or carrier) to form a solid preformulated composition comprising a homogeneous mixture of compounds of the present invention. When referring to these preformulated compositions as homogeneous, it means that the active ingredient is uniformly dispersed throughout the composition so that the composition can be readily subdivided into an equally effective unit dosage form such as a tablet, a pill and a capsule.

The tablet or pill of the present invention may be coated or otherwise compounded to provide a dosage form with an advantage of a prolonged action, or an action of protecting the tablet or pill from acidic conditions in stomach. For example, the tablet or pill may include an internal dose component and an external dose component, the latter having a form of a sheath over the former. An enteric layer may be used to separate the two components, wherein the enteric layer serves to prevent disintegration in the stomach and allow the inner component to intactly pass into duodenum or for a delayed release. A variety of materials may be used for such enteric layer or coating, including a number of polymeric acids and a mixture of polymeric acid with such materials as shellac, cetyl alcohol, and cellulose acetate.

Compositions for inhalation or insufflation include a solution, suspension and pulvis in a pharmaceutically acceptable aqueous solvent or organic solvent, or a mixture thereof. Liquid or solid compositions may include a suitable pharmaceutical excipient. Preferably, these compositions are administered by an oral or nasal respiratory route for a local or systemic effect. Compositions in a preferred pharmaceutically acceptable solvent may be nebulized by use of an inert gas. The nebulized solution may be inhaled directly from a nebulizing device, or the nebulizing device may be attached to a mask mesh, or an intermittent positive pressure breathing machine. Solution, suspension, or pulvis compositions may be administered by a device that delivers the dosage form in an appropriate manner, preferably by the oral or nasal route.

Based on this, the present invention further provides an antiviral spray, which includes tannic acid as an active ingredient.

Further, the antiviral spray includes the following components in parts by weight: 5 to 20 parts of tannic acid, 1 to 50 parts of a polyphenolic compound, 1 to 15 parts of an additament, and water as the rest.

The present invention further provides an antiviral aerosol, which includes tannic acid as an active ingredient.

Further, the antiviral aerosol includes the following components in parts by weight: 1 to 20 parts of tannic acid, 0 to 10 parts of an antiviral metal salt, 1 to 15 parts of an additament, and a propellant as the rest.

Further, the propellant is tetrafluoroethane (HFA-134a) or heptafluoropropane (HFA-227).

The present invention further provides an antiviral oral preparation, which includes tannic acid as an active ingredient.

Further, the antiviral oral preparation includes the following components in parts by weight: 3 to 20 parts of tannic acid, 1 to 15 parts of an antiviral metal salt, 1 to 15 parts of an additament, and water as the rest.

Further, the additament includes an antioxidant and other pharmaceutically acceptable auxiliary materials.

Further, the antioxidants include vitamin C and rosmarinic acid.

The present invention has the following beneficial effects.

Research results of the present invention show that tannic acid has a significant inhibitory effect on respiratory viruses including SARS-CoV-2 coronavirus, Influenza A H1N1 virus, etc., with an exact curative effect, and thus has a broad application prospect in the field of preparation of medicaments against respiratory viruses. In addition, tannic acid exists in a variety of plants, which is a natural active compound existing in nature, and has also been used as a food additive, with a high safety and good foundation for medicament development.

DETAILED DESCRIPTION

The present invention is further described below in conjunction with specific embodiments, but the embodiments do not limit the present invention in any form. Unless otherwise specified, reagents, methods and equipment used in the present invention are conventional reagents, methods and equipment in the technical field.

Active virus experiments of the present invention are all entrusted to Guangdong Provincial Center for Disease Control and Prevention to perform, and microbial materials are provided by Guangdong Provincial Center for Disease Control and Prevention.

Unless otherwise specified, the reagents and materials used in the following embodiments are commercially available.

Embodiment 1: Determination of Toxicity of Tannic Acid to African Green Monkey Kidney Cells (Vero-E6 Cells)

1. Experimental Materials
    (1) Medicaments: experimental group, tannic acid; control group, Remdesivir (purchased from Shanghai Top-Science Technology Co., Ltd.);
    (2) Cell line: African green monkey kidney cells (Vero-E6 cells);
    (3) Others: MEM medium; 96-well culture plate.
2. Experimental steps
    (1) Cell culture was carried out by a microculture method.
    (2) Medicament dilution: tannic acid and Remdesivir in 12 centrifuge tubes was respectively times diluted to in total 12 concentrations of tannic acid and Remdesivir solutions with a cell culture medium [component requirements: MEM medium (Gibco Invitrogen), 1% double antibody (Gibco Invitrogen), 2% fetal bovine serum (FBS; Gibco Invitrogen)].
    (3) Three parallel wells were set for each concentration, and cell control wells were set at the same time (without medicament, with culture medium only).
    (4) After 48 hours, 10 ul of CCK-8 was added to each 100 ul of cell culture medium, incubated at 37° C. for 1 hour, and OD450 was measured with a spectrophotometer, and a maximum non-toxic concentration ($TC_0$) and a median toxic concentration ($TC_{50}$) of tannic acid and Remdesivir were calculated.
3. Experimental results

TABLE 1

Determination results of toxicity of tannic acid and Remdesivir to African green monkey kidney cells

| Group | $TC_0$ (μM) | $TC_{50}$ (μM) |
| --- | --- | --- |
| Tannic acid | 11.8 | 23.5 |
| Remdesivir | 52.8 | 105.6 |

Embodiment 2: Efficacy Test of Tannic Acid Against SARS-CoV-2 Virus

1. Experimental materials
    (1) Medicaments: experimental group, tannic acid; control group, Remdesivir (purchased from Shanghai Top-Science Technology Co., Ltd.);
    (2) Cell line: African green monkey kidney cells (Vero-E6 cells);
    (3) Virus: SARS-CoV-2 virus;
    (4) Others: MEM medium; 96-well culture plate.
2. Experimental steps
    (1) Vero-E6 cells were pre-cultured into monolayer cells in a 96-well culture plate (a number of cells: $2\times10^4$ cells/well);
    (2) The medicament solution with the maximum non-toxic dose ($TD_0$) was selected as the medicament to be tested, and was respectively times diluted to 12 concentrations with a cell maintenance solution, and a virus infection titer is 100 $TCID_{50}$;
    (3) There were 3 wells for each concentration of the medicament. After the virus was adsorbed for 1 hour, the virus solution was discarded. After washing once with PBS, each well was supplemented with 0.2 ml of maintenance solution containing the medicament. At the same time, a cell control (with maintenance solution only), medicament control (without virus) and virus control (without medicament solution) were set, and cultured in a 37° C., 5% $CO_2$ incubator.
    (4) After 48 hours, a cell culture supernatant was collected for viral nucleic acid extraction, and a relative quantification of the viruses was carried out using a COVID-19 fluorescence quantitative PCR kit (already obtained a clinical medical device registration certificate), and an effect of tannic acid on inhibition of SARS-CoV was calculated; parameters such as median inhibitory concentration ($IC_{50}$) and a selection index (SI) were calculated.

Selection Index (SI)=$TC_{50}/IC_{50}$ $TC_{50}$ (50% toxic concentration): calculated by Reed-Muench formula $IC_{50}$ (median inhibitory concentration): calculated by Reed-Muench formula 3. Experimental results As shown in Table 2, tannic acid shows a relatively high antiviral activity against SARS-CoV-2 virus with an IC50 value against SARS-CoV-2 virus being 0.0032 μM and a SI being 7343.75, which is significantly higher than an antiviral activity of the positive control group Remdesivir, and tannic acid also has a relatively high selection index.

TABLE 2

Activity parameters of tannin acid and Remdesivir against viruses

| Group | $IC_{50}$ (μM) | SI |
| --- | --- | --- |
| Tannic acid | 0.0032 ± 0.0002** | 7343.75 |
| Positive control (Remdesivir) | 0.651 ± 0.013* | 162.21 |

Note:
Compared with the positive control group, *P < 0.05, **P < 0.01.

Embodiment 3: Determination of Toxicity of Tannic Acid to Canine Kidney Epithelial Cells (MDCK Cells)

1. Experimental materials
   (1) Medicaments: experimental group, tannic acid; control group, Ribavirin (purchased from ROMIT Pharmaceutical Corporation Jiangsu);
   (2) Cell line: canine kidney epithelial cells (MDCK cells);
   (3) Others: DMEM medium; 96-well culture plate.
2. Experimental steps
   (1) Cell culture was carried out by a microculture method.
   (2) Medicament dilution: tannic acid and Ribavirin in 12 centrifuge tubes was respectively times diluted to in total 12 concentrations of tannic acid and Ribavirin solutions with a cell culture medium [component requirements: DMEM medium (Gibco Invitrogen), 1% double antibody (Gibco Invitrogen), 10% fetal bovine serum (FBS; Gibco Invitrogen)].
   (3) Medicaments of each dilution were added into wells of MDCK cells, 3 wells for each dilution, 100 μL per well, and normal cell control wells were set at the same time, and cultured in a 37° C., 5% $CO_2$ incubator.
   (4) Cytopathic changes were observed and recorded every day: (−), no cytopathic changes; (+), 0 to ¼ of cells were cytopathic; (++), ¼ to ½ of cells were cytopathic; (+++), ½ to ¾ of cells were cytopathic; (++++), ¾ to 1 of cells were cytopathic. The maximum non-toxic concentration ($TC_0$) of the medicament was taken as the minimum dilution times of the medicament without cytopathic changes, and the median toxic concentration ($TC_{50}$) of the medicament was calculated by the Reed-Muench formula.
3. Experimental results

TABLE 3

Determination results of toxicity of tannic acid and Ribavirin to canine renal epithelial cells

| Group | $TC_0$ (μM) | $TC_{50}$ (μM) |
| --- | --- | --- |
| Tannic acid | 376.21 | 752.41 |
| Ribavirin | 655.17 | 1310.34 |

Embodiment 4: Efficacy Test of Tannic Acid Against Influenza a H1N1 Virus

1. Experimental materials:
   (1) Medicaments: experimental group, tannic acid; control group, Ribavirin (purchased from ROMIT Pharmaceutical Corporation Jiangsu);
   (2) Cell line: canine kidney epithelial cells (MDCK cells);
   (3) Virus: Influenza A H1N1 virus;
   (4) Others: DMEM medium; 96-well culture plate.
2. Experimental steps
   (1) Monolayer MDCK cells were digested with 0.25% trypsin, inoculated and cultured at a cell concentration of 1×10⁵ cells/mL, and the culture medium was taken away when the cells grew to a desired density (80% to 90%), and washed twice with PBS;
   (2) They were divided into cell group, virus group, Ribavirin group and tannic acid group, a medicament solution with the maximum non-toxic dose ($TD_0$) was selected as the medicament to be tested, and prepared into 12 concentrations of medicament-containing serum after times diluted;
   (3) 100 $TCID_{50}$/100 μL Influenza A H1N1 virus was used to infect cells of each group (the cell group was not infected, but added with 100 μL of a maintenance solution); after incubator adsorption, PBS washing and other operations, Ribavirin serum, tannic acid serum, and cell maintenance solution was added respectively, 3 wells of each medicament concentration, 100 μL/well, cultured in a 37° C., 5% $CO_2$ incubator;
   (4) After 48 hours, the cell culture supernatant was collected for viral nucleic acid extraction, and a relative quantification of the viruses was carried out using an influenza A H1N1 fluorescence quantitative PCR kit, and an effect of tannic acid on inhibition of A H1N1 virus was calculated; parameters such as median inhibitory concentration ($IC_{50}$) and selection index (SI) were calculated.

Selection Index (SI)=$TC_{50}/IC_{50}$ $TC_{50}$ (50% toxic concentration): calculated by Reed-Muench formula $IC_{50}$ (median inhibitory concentration): calculated by Reed-Muench formula 3. Experimental Results As shown in Table 4, tannic acid showed a relatively high antiviral activity against influenza A H1N1 virus with an $IC_{50}$ value against influenza A H1N1 virus being 0.0032 μM and a SI being 7343.75, which is significantly higher than an antiviral activity of the positive control group Ribavirin, and tannic acid also has a relatively high selection index.

TABLE 4

Activity parameters of tannic acid and Ribavirin against viruses

| Group | $IC_{50}$ (μM) | SI |
| --- | --- | --- |
| Tannic acid | 0.17 ± 0.02** | 4425.94 |
| Positive control (Ribavirin) | 22.60 ± 0.04* | 57.98 |

Note:
Compared with the positive control group, *P < 0.05, **P < 0.01.

Embodiment 5: Determination of Toxicity of Tannic Acid Composition to African Green Monkey Kidney Cells (Vero-E6 Cells)

1. Experimental materials
   (1) Medicaments: in the experimental group, tannic acid was mixed with catechin, resveratrol, and zinc gluconate according to a mass ratio of 1:1 to prepare into three pharmaceutical compositions; in the control group, Remdesivir (purchased from Shanghai TopScience Technology Co., Ltd.);
   (2) Other experimental materials were the same as those in Embodiment 1.
2. Experimental steps: refer to Embodiment 1.
3. Experimental results

TABLE 5

Determination results of toxicity of tannic acid compositions to African green monkey kidney cells

| Group | $TC_0$ (μg/ml) | $TC_{50}$ (μg/ml) |
|---|---|---|
| Tannic acid + catechin | 21.562 | 43.132 |
| Tannic acid + resveratrol | 22.177 | 44.350 |
| Tannic acid + zinc gluconate | 15.132 | 30.265 |
| Remdesivir | 31.816 | 63.633 |

Embodiment 6: Efficacy Test of Tannic Acid Compositions Against SARS-CoV-2

1. Experimental materials
   (1) Medicaments: same as Embodiment 5;
   (2) Other experimental materials were the same as those in Embodiment 2.
2. Experimental procedure: refer to Embodiment 2.
3. Experimental results:

As shown in Table 6, the tannic acid compositions show a relatively high antiviral activity against SARS-CoV-2 virus, which is significantly higher than an antiviral activity of the positive control group Remdesivir, and the tannic acid compositions also have a relatively high selection index.

TABLE 6

Activity parameters of tannic acid compositions against SARS-CoV-2 virus

| Group | $IC_{50}$ (μg/ml) | SI |
|---|---|---|
| Tannic acid + catechin | 0.00412 ± 0.00003** | 10468.93 |
| Tannic acid + resveratrol | 0.00335 ± 0.00004* | 13238.81 |
| Tannic acid + zinc gluconate | 0.00124 ± 0.00007** | 24407.26 |
| Remdesivir | 0.392 ± 0.003** | 162.21 |

Note:
Compared with the positive control group, *$P < 0.05$, **$P < 0.01$.

Embodiment 7: Determination of Toxicity of Tannic Acid Compositions to Canine Kidney Epithelial Cells (MDCK Cells)

1. Experimental materials
   (1) Medicaments: same as Embodiment 5;
   (2) Other experimental materials were the same as those in Embodiment 3.
2. Experimental procedure: refer to Embodiment 3.
3. Experimental results

TABLE 7

Determination results of toxicity of tannic acid compositions and Ribavirin to canine renal epithelial cells

| Group | $TC_0$ (μg/ml) | $TC_{50}$ (μg/ml) |
|---|---|---|
| Tannic acid + catechin | 650.01 | 1300.56 |
| Tannic acid + resveratrol | 665.43 | 1330.68 |
| Tannic acid + zinc gluconate | 573.35 | 1147.21 |
| Ribavirin | 160.00 | 320.01 |

Embodiment 8: Efficacy Test of Tannic Acid Compositions Against Influenza a H1N1 Virus 1. Experimental materials
   (1) Medicaments: for the experimental group, same as Embodiment 5; for the control group, same as Embodiment 4;
   (2) Other experimental materials were the same as those in Embodiment 4.
2. Experimental procedure: refer to Embodiment 4.
3. Experimental results As shown in Table 8, the tannic acid compositions show a relatively high antiviral activity against influenza A H1N1 virus, which is significantly higher than an antiviral activity of the positive control group Ribavirin, and the tannic acid compositions also have a relatively high selection index.

TABLE 8

Activity parameters of tannic acid compositins and Ribavirin against viruses

| Group | $IC_{50}$ (μg/ml) | SI |
|---|---|---|
| Tannic acid + catechin | 0.24 ± 0.02** | 5419.00 |
| Tannic acid + resveratrol | 0.19 ± 0.01** | 7003.58 |
| Tannic acid + zinc gluconate | 0.11 ± 0.01** | 10429.20 |
| Ribavirin | 5.52 ± 0.03* | 57.98 |

Note:
Compared with the positive control group, *$P < 0.05$, **$P < 0.01$.

Embodiment 9: An Antiviral Spray

An antiviral spray includes the following components in weight percentages: 10% of tannic acid, 5% of catechin, 3% of vitamin C, and deionized water as the rest.

Embodiment 10: An Antiviral Spray

An antiviral spray includes the following components in weight percentages: 5% of tannic acid, 5% of resveratrol, 3% of rosmarinic acid, and deionized water as the rest.

Embodiment 11: An Antiviral Aerosol

An antiviral aerosol includes the following components in weight percentages: 5% of tannic acid, 1% of zinc gluconate, 8% of deionized water, 2% of ethanol, and a propellant tetrafluoroethane as the rest.

Embodiment 12: An Antiviral Oral Preparation

An antiviral oral preparation includes the following components in weight percentages: 10% of tannic acid, 10% of zinc gluconate, 2% of an adjuvant, and distilled water as the rest.

The above-mentioned embodiments are preferred embodiments of the present invention, but the implementations of the present invention are not limited by the above-mentioned embodiments, and any other changes, modifications, substitutions, combinations, and simplifications should be equivalent replacement manners, which are all included in the protection scope of the present invention.

What is claimed is:

1. A method of using a medicament against a novel coronavirus SARS-COV-2, wherein the method comprises:
   preparing a medicament comprising tannic acid and zinc gluconate, wherein a mass ratio of the tannic acid to the zinc gluconate is 1:1; and
   administering the medicament to a patient infected with the novel coronavirus SARS-CoV-2.

2. The method according to claim 1, wherein the medicament further comprises a pharmaceutically acceptable adjuvant.

3. The method according to claim 2, wherein the medicament is an oral preparation.

4. The method according to claim 2, wherein the medicament is a spray.

5. The method according to claim 2, wherein the medicament is an aerosol.

6. The method according to claim 2, wherein the medicament is an injection.

7. The method according to claim 3, wherein the oral preparation is a tablet or a capsule.

8. The method according to claim 2, wherein the medicament is an inhalant.

* * * * *